US009817248B2

(12) United States Patent
Yang et al.

(10) Patent No.: US 9,817,248 B2
(45) Date of Patent: Nov. 14, 2017

(54) METHOD OF VIRTUALLY TRYING ON EYEGLASSES

(71) Applicant: MULTIMEDIA IMAGE SOLUTION LIMITED, Dublin (IE)

(72) Inventors: Ping Yang, Hangzhou (CN); YanQing Lu, Hangzhou (CN); Jin Wang, Hangzhou (CN)

(73) Assignee: MULTIMEDIA IMAGE SOLUTION LIMITED, Dublin (IE)

( * ) Notice: Subject to any disclaimer, the term of this patent is extended or adjusted under 35 U.S.C. 154(b) by 227 days.

(21) Appl. No.: 14/582,086

(22) Filed: Dec. 23, 2014

(65) Prior Publication Data

US 2016/0178936 A1 Jun. 23, 2016

(51) Int. Cl.

| A61B 3/00 | (2006.01) |
| G02C 13/00 | (2006.01) |
| A61B 3/04 | (2006.01) |
| G06T 19/00 | (2011.01) |
| G06F 3/01 | (2006.01) |
| G06T 11/60 | (2006.01) |
| G06T 17/00 | (2006.01) |
| G06T 19/20 | (2011.01) |

(52) U.S. Cl.
CPC ............ *G02C 13/003* (2013.01); *A61B 3/04* (2013.01); *G06F 3/012* (2013.01); *G06T 11/60* (2013.01); *G06T 17/00* (2013.01); *G06T 19/006* (2013.01); *G06T 19/20* (2013.01); *G06T 2210/16* (2013.01); *G06T 2219/2004* (2013.01)

(58) Field of Classification Search
CPC ....... G02C 13/003; G02C 7/027; G06F 3/012; G06T 7/0042; G06T 11/60; G06T 19/006; G06T 2200/04; G06T 2207/30041; G06T 2207/30201; A61B 3/04
USPC ........................... 351/246, 159.75, 204, 212
See application file for complete search history.

(56) References Cited

U.S. PATENT DOCUMENTS

| 5,159,361 | A * | 10/1992 | Cambier ................ A61B 3/107 351/212 |
| 8,733,936 | B1 * | 5/2014 | Kornilov .................. A61B 3/10 351/159.75 |
| 2003/0123026 | A1 * | 7/2003 | Abitbol .............. G06Q 30/0641 351/204 |
| 2013/0321412 | A1 * | 12/2013 | Coon ...................... G06T 17/00 345/420 |

(Continued)

*Primary Examiner* — Bumsuk Won
*Assistant Examiner* — Collin X Beatty
(74) *Attorney, Agent, or Firm* — Winston Hsu

(57) ABSTRACT

A method of virtually trying on eyeglasses includes capturing a plurality of images of a user's face, obtaining locations of a plurality of feature points on the user's face in the plurality of images, and using the locations of the plurality of feature points in the plurality of images to create a standard three-dimensional model of the user. Next, a selection is received from the user of a pair of virtual eyeglasses, the selected pair of virtual eyeglasses having a corresponding three-dimensional model depicting the size and shape of the selected pair of virtual eyeglasses. After this, a modified three-dimensional model of the user having the selected pair of virtual eyeglasses superimposed on the user's face is created according to the standard three-dimensional model of the user and the corresponding three-dimensional model of the selected pair of virtual eyeglasses. The result is then displayed for the user to see.

10 Claims, 24 Drawing Sheets

(56) References Cited

U.S. PATENT DOCUMENTS

2014/0118500 A1* 5/2014 Liu .................... H04N 13/0203
                                                    348/46

* cited by examiner

METHOD OF VIRTUALLY TRYING ON EYEGLASSES

BACKGROUND OF THE INVENTION

1. Field of the Invention

The invention relates to image processing, and more particularly, to a method of image processing for allowing a user to virtually try on eyeglasses in order to select a style of eyeglasses that is appealing to the user.

2. Description of the Prior Art

In recent times a significant percentage of people now wear eyeglasses, either for correcting vision or for serving as a fashion accessory. At the same time, there are now an almost limitless number of eyeglasses being sold, and these eyeglasses come in different styles and sizes. Consequently, consumers now have a large variety of eyeglasses to choose from, and can pick exactly the style of eyeglasses that best suit them. Although eyeglasses stores are common, eyeglasses stores are limited in the number of different eyeglass frames that they are able to display inside the store at any one time. Consumers may find themselves disappointed by the limited eyeglasses options within stores, and may need to visit numerous stores in order to find just the right style of eyeglasses.

Furthermore, consumers are now shopping online more than ever before, and online stores can offer a much greater selection of eyeglasses styles than traditional brick and mortar retail stores are able to. However, the problem with shopping online is customers are not able to try on the various types of eyeglasses in order to see if the eyeglasses are the right size and style for the customer. This leads to customers having to make an uninformed decision as to whether the eyeglasses are appropriate for them or not. Often times the customer will regret the decision to buy a particular pair of eyeglasses online after the customer has received the eyeglasses. To make matters worse, if prescription lenses for the eyeglasses have already been cut and installed in the frames of the eyeglasses, there is no easy way for the customer to return the eyeglasses without losing the money used to pay for the lenses. Consequently, there is a need for a better way to shop for eyeglasses.

SUMMARY OF THE INVENTION

It is therefore one of the primary objectives of the claimed invention to provide a method of allowing a user to virtually try on eyeglasses in order to select a style of eyeglasses that is appealing to the user.

According to an exemplary embodiment of the claimed invention, a method of virtually trying on eyeglasses is disclosed. The method includes capturing a plurality of images of a user's face, obtaining locations of a plurality of feature points on the user's face in the plurality of images, and using the locations of the plurality of feature points in the plurality of images to create a standard three-dimensional model of the user. Next, a selection is received from the user of a pair of virtual eyeglasses, the selected pair of virtual eyeglasses having a corresponding three-dimensional model depicting the size and shape of the selected pair of virtual eyeglasses. After this, a modified three-dimensional model of the user having the selected pair of virtual eyeglasses superimposed on the user's face is created according to the standard three-dimensional model of the user and the corresponding three-dimensional model of the selected pair of virtual eyeglasses. The resulting modified three-dimensional model of the user having the selected pair of virtual eyeglasses superimposed on the user's face is then displayed.

It is an advantage that the present invention provides a way for the user to virtually try on different styles of eyeglasses without actually having to travel to an eyeglasses store. This allows the user to shop online for eyeglasses, thereby saving the user time and also enabling the user to browse a much larger selection of different eyeglasses styles and sizes. Furthermore, by using three-dimensional modeling, the user will be given a chance to see exactly how the eyeglasses will look on the user.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
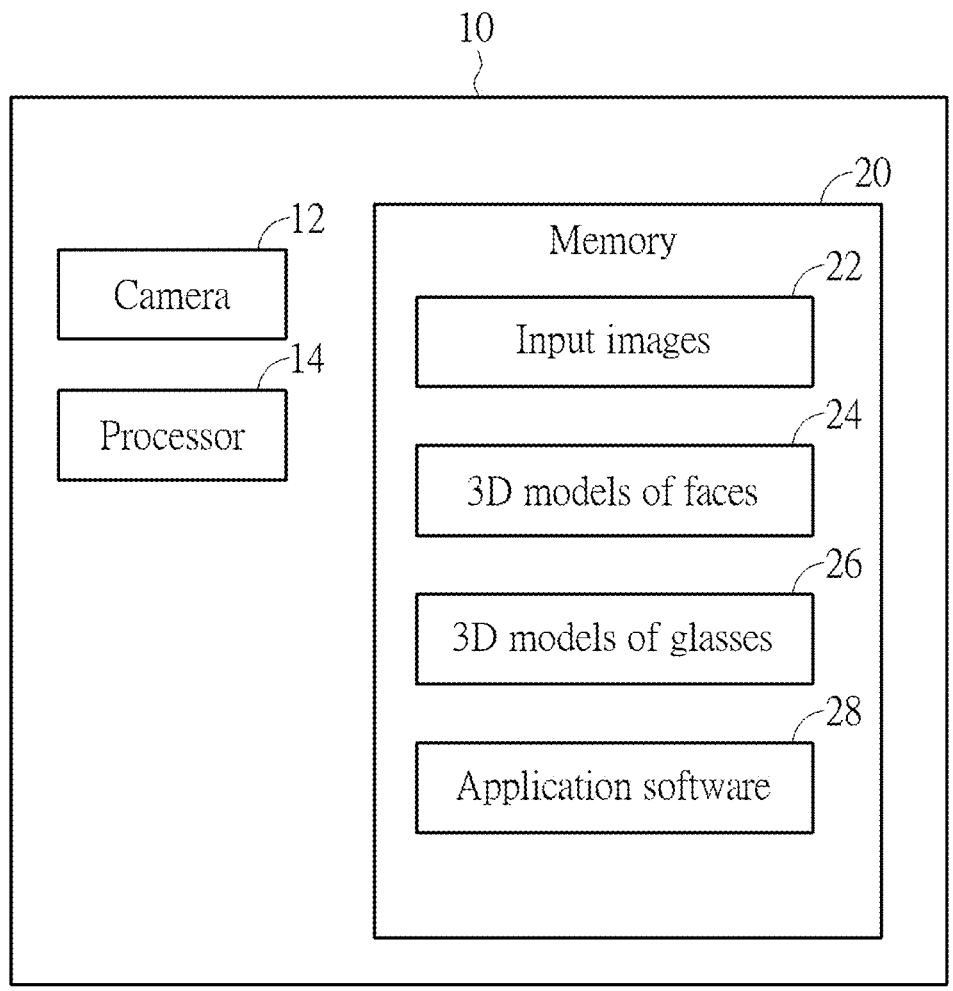
FIG. 1 is a block diagram of a system for implementing the present invention method of virtually trying on eyeglasses.

Please refer to FIG. 1. FIG. 1 is a block diagram of a system 10 for implementing the present invention method of virtually trying on eyeglasses. The system 10 comprises a camera 12, a processor 14 for executing commands of the system 10, and a memory 20 for storing data and program code. The memory 20 stores a plurality of input images 22 that are images of a user captured using the camera 12. These input images 22 are then used to create a three-dimensional model of the user's face that is stored in memory in a section reserved for three-dimensional models of faces 24. The memory 20 also stores three-dimensional models for various types of eyeglasses in a section reserved for three-dimensional models of eyeglasses 26. The memory 20 additionally stores application software 28 that is used for creating the three-dimensional models of faces 24 based on the input images 22 and for performing image processing for superimposing a selected one of the three-dimensional models of eyeglasses 26 over a user's three-dimensional face model indicated by the three-dimensional models of faces 24. The system 10 can be implemented in a computer in which the camera 12 is a webcam, can be implemented in a mobile phone in which the camera 12 uses the mobile phone's camera, can be implemented in a digital camera, and in other electronic devices having both a camera for capturing images and a display for displaying the results. The application software 28 can be written in a language that is easily portable to a wide variety of platforms to ensure that the present invention method can be universally applied across platforms.

Figure 2:
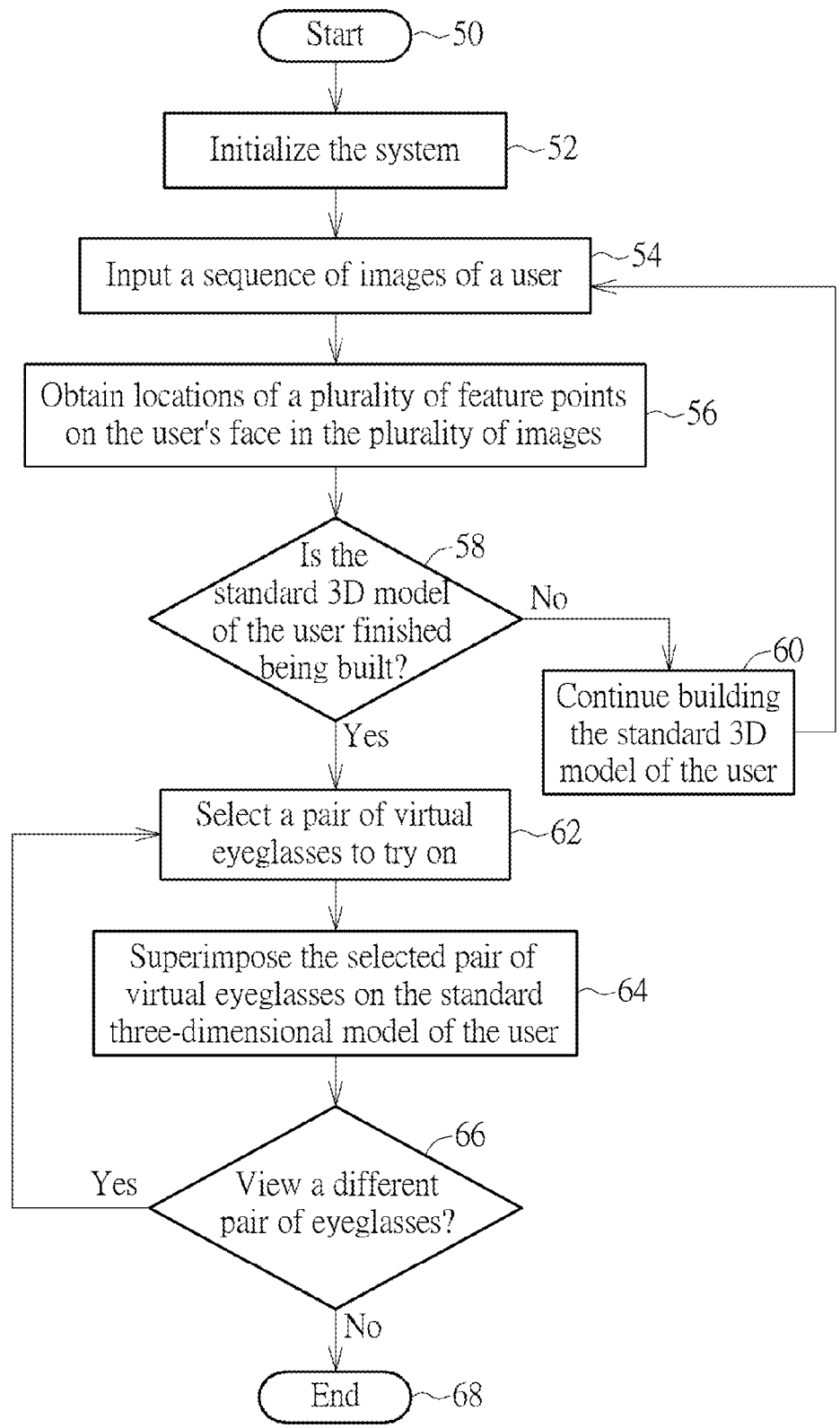
FIG. 2 is a flowchart describing the method of performing the method of method of virtually trying on eyeglasses according to the present invention.

Please refer to FIG. 2. FIG. 2 is a flowchart describing the method of performing the method of method of virtually trying on eyeglasses according to the present invention. Steps in the flowchart will be explained as follows.

Step 50: Start.

Step 52: Initialize the system 10.

Step 54: Input a sequence of images of a user. The images may be captured using the camera 12.

Step 56: Obtain locations of a plurality of feature points on the user's face in the plurality of images.

Step 58: Determine if a standard three-dimensional model of the user is finished being built according to the images of the user and the locations of the plurality of feature points. If so, go to step 62. If not, go to step 60.

Step 60: Continue building the standard three-dimensional model of the user, and go back to step 54.

Step 62: The user selects a pair of virtual eyeglasses to try on, the pair of virtual eyeglasses having a corresponding three-dimensional model depicting the size and shape of the selected pair of virtual eyeglasses.

Step 64: Superimpose the selected pair of virtual eyeglasses on the standard three-dimensional model of the user in order to illustrate what the user would look like if the user were wearing the selected pair of virtual eyeglasses. The result is a modified three-dimensional model of the user, which is then displayed to the user.

Step 66: Determine if the user wishes to view a different pair of eyeglasses. If so, go back to step 62. If not, go to step 68.

Step 68: End.

The present invention produces a virtual picture of the user in which an image of a selected pair of virtual eyeglasses is superimposed on the user's face according to the standard three-dimensional model of the user and the corresponding three-dimensional model of the selected pair of virtual eyeglasses. Once the standard three-dimensional model of the user is created, the modified three-dimensional model of the user can be generated quickly after the user selects the pair of virtual eyeglasses to try on. Since the standard three-dimensional model of the user is built using the locations of the plurality of feature points on the user's face in the plurality of images and since the corresponding three-dimensional model of the selected pair of virtual eyeglasses also contains location information regarding where the selected pair of virtual eyeglasses is placed on the user's face, the modified three-dimensional model of the user represents a true indication of how the selected pair of virtual eyeglasses would look on the user.

First of all, in order to superimpose the virtual eyeglasses on the user's face, the standard three-dimensional model of the user needs to be calculated. Based on the standard three-dimensional model of the user, not only can the exact location on the user's face for the superimposed virtual eyeglasses be determined, but also the overlap between the superimposed virtual eyeglasses and the face can be dealt with as well.

Since each user's face has unique features, multiple feature points on the face are sampled. Each feature point represents the different characteristics of the user's face, such as the corners and outer edges of the eyes, corners and outer edges of the mouth, corners and outer edges of the nose, outer edges of the eyebrows, and outer edges of the face. After obtaining the locations of the plurality of the features points on the user's face in the plurality of captures images of the user, the standard three-dimensional model M of the user can be calculated using all of this data taken as a whole. Each captured image of the user will slightly differ from the standard three-dimensional model M of the user due to differences in the rotation of the user's face and the horizontal displacement of the user's face.

Figure 3:
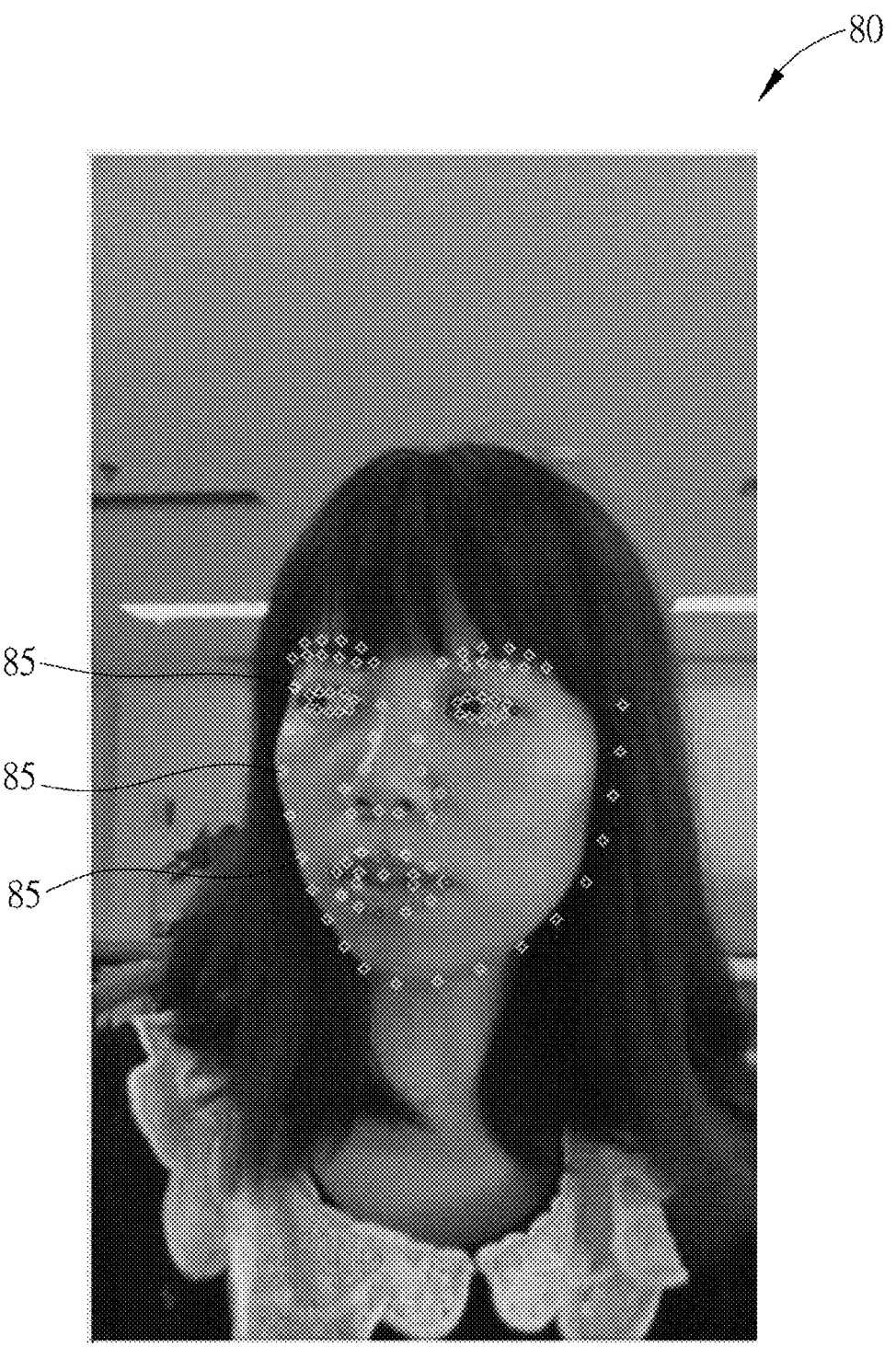
FIG. 3 is an image illustrating a user whose face is rotated a first direction.
Figure 4:
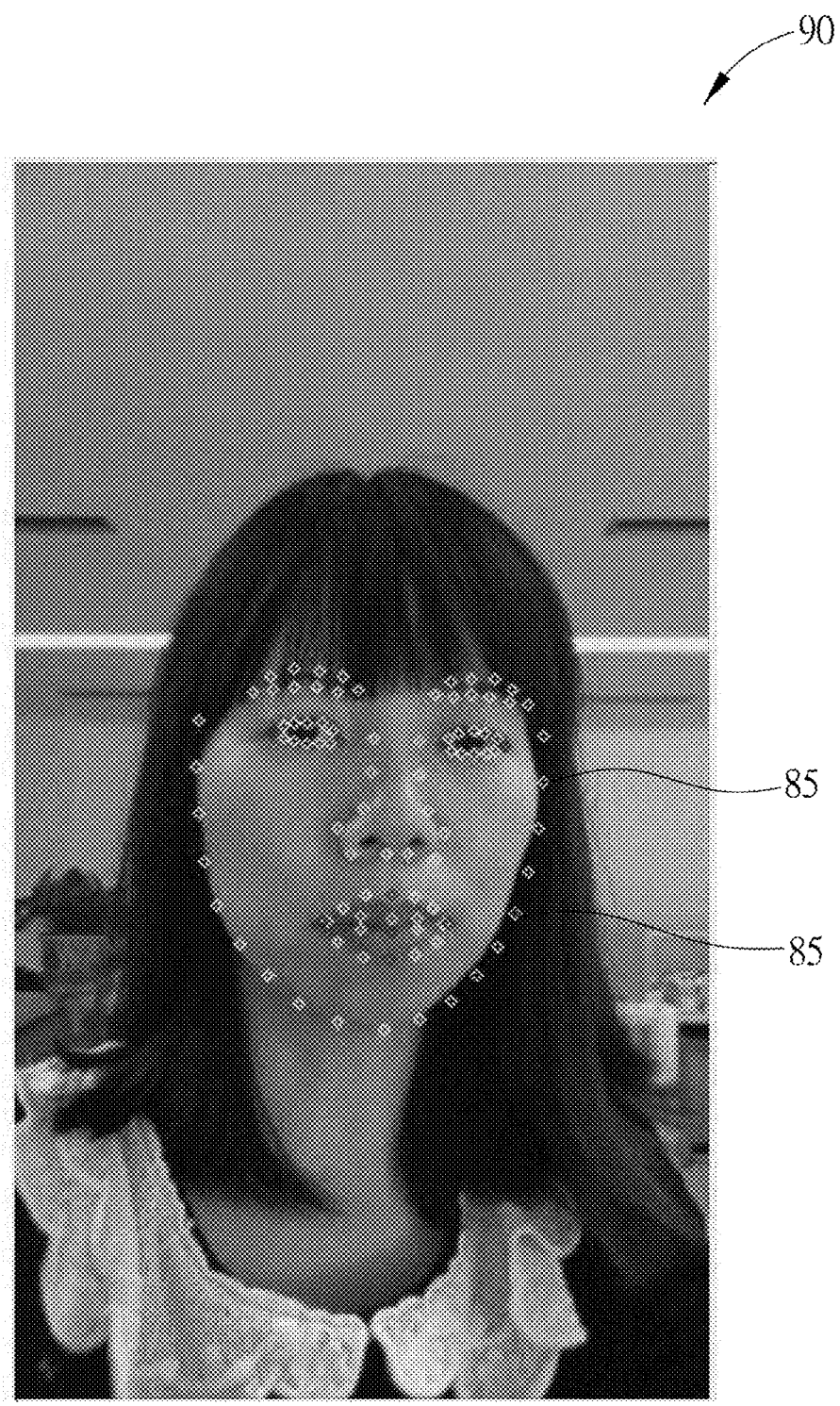
FIG. 4 is an image illustrating the user whose face is rotated a second direction.

Please refer to FIG. 3 and FIG. 4. FIG. 3 is an image 80 illustrating a user whose face is rotated a first direction, and FIG. 4 is an image 90 illustrating the user whose face is rotated a second direction. In images 80 and 90 many different feature points 85 are shown on the user's face for obtaining key facial features of the user. When capturing a plurality of images of the user's face, preferably the user maintains a same facial expression in each image as the user's face is rotated while the position of the camera 12 is fixed. In this way, multiple pictures can be taken of the user's face from different rotation angles while the user's facial expression does not change. This allows the face to be modeled as a rigid rotating object, and thereby allows the standard three-dimensional model M of the user to be calculated. Preferably ten or more images of the user are captured. At least 8 feature points 85 should be used, and preferably the number of feature points 85 used is approximately 95, which offers a good balance of a high number of feature points 85 while at the same time limiting the amount of calculations needed to generate the standard three-dimensional model M of the user. The location of a specific feature point is fixed from one captured image to the next. For instance, if a feature point corresponds to the inside corner of the user's left eye in one image, the same feature point will still correspond to the inside corner of the user's left eye in all other images.

How to decide exactly which locations on the user's face should be chosen for being feature points is disclosed in other patents assigned to the applicant of the present invention, including U.S. Pat. Nos. 7,953,253 and 8,295,557, each of which is incorporated by reference in its entirety.

The standard three-dimensional model M of the user is calculated using n three-dimensional feature points P, and the collection of these points can be represented as $\{P^{(k)}\}_{k=1}^{n}$. When the user's face is rotating as the images of the user's face are being captured, the equation RM+t can be used to represent the three-dimensional model of the user in any given image, where R represents the rotation of the user's face in an image, and t represents the horizontal displacement of the user's face in the image. Therefore, when trying to calculate RM+t, it is necessary to calculate the coordinates of all the points $\{P^{(k)}\}^{k=1}_n$ at a given rotation R and horizontal displacement t.

Figure 5:
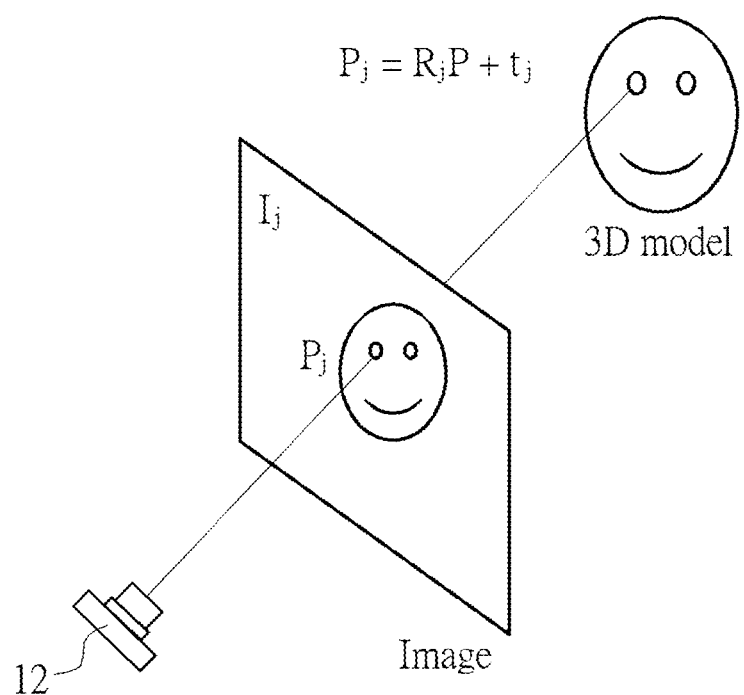
FIG. 5 illustrates representing the three-dimensional model of the user in an image.
Figure 6:
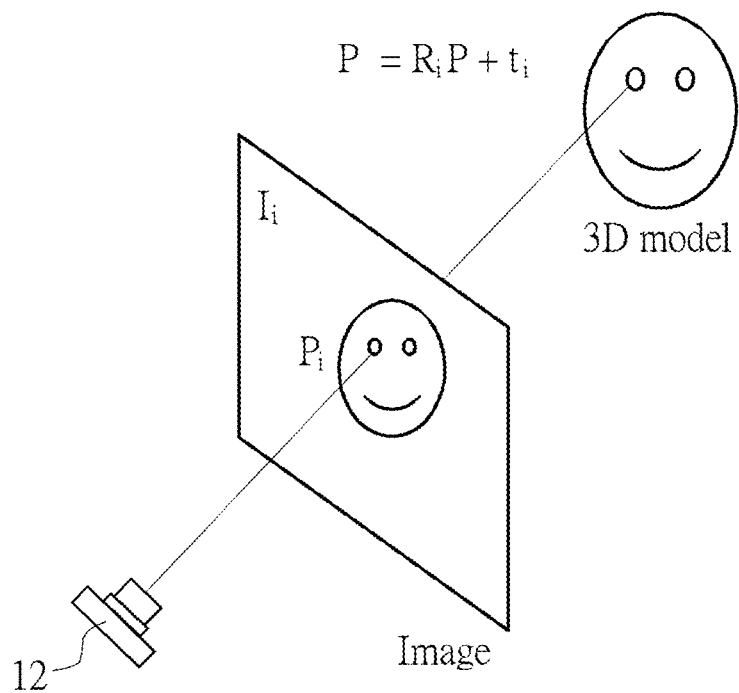
FIG. 6 illustrates representing the three-dimensional model of the user in another image.

Please refer to FIG. 5 and FIG. 6. FIG. 5 illustrates representing the three-dimensional model of the user in image $I_j$. FIG. 6 illustrates representing the three-dimensional model of the user in image $I_i$. In FIG. 5 image $I_j$ is captured by the camera 12, and a point $P_j$ on the image $I_j$ can be calculated according to the equation $P_j=R_j*P+t_j$. Similarly, in FIG. 6 image $I_i$ is captured by the camera 12, and a point $P_i$ on the image $I_i$ can be calculated according to the equation $P_i=R_i*P+t_i$. Points $P_j$ and $P_i$ represent points on the three-dimensional model of the user according to the rotation and horizontal displacement that occurs in the respective images. The variables $R_j$ and $R_i$ represent the rotation of the user's face in images $I_j$ and $I_i$, respectively. Similarly, the variables $t_j$ and $t_i$ represent the horizontal displacement of the user's face in images $I_j$ and $I_i$, respectively.

The three-dimensional coordinates of a certain point $P^{(k)}$ can be represented as $(P_x^{(k)}, P_y^{(k)}, P_z^{(k)})$. When the camera 12 captures image $I_j$, the three-dimensional model of the user in image $I_j$ can be calculated as being equal to $R_jM+t_j$. From this, the updated three-dimensional coordinates of $P^{(k)}$ can be calculated as $(P_x^{(k)\prime}, P_y^{(k)\prime}, P_z^{(k)\prime})^T = R_j(P_x^{(k)}, P_y^{(k)}, P_z^{(k)})^T + t_j$, where T indicates a matrix transpose function for reflecting a matrix over its main diagonal, and which is symbolized by $[A^T]_{ij}=[A]_{ji}$. If the updated points $P^{(k)}$ in image $I_j$ are $p_j^{(k)}$, and the two-dimensional coordinates of $p_j^{(k)}$ are $(p_{j,x}^{(k)}, p_{j,y}^{(k)})$, are then according to the aperture imaging principle, the three-dimensional coordinates of point $P^{(k)}$ are equal to $(P_x^{(k)}, P_y^{(k)}, P_z^{(k)})$ and the two-dimensional model $(p_{j,x}^{(k)}, p_{j,y}^{(k)})$ of point $p_j^{(k)}$ satisfy the relationship given in equation (1):

$$\left(P_{j,x}^{(k)}, P_{j,y}^{(k)}, 1\right) = A\left(\frac{P_x^{(k)\prime}}{P_z^{(k)\prime}}, \frac{P_y^{(k)\prime}}{P_z^{(k)\prime}}, 1\right)^T, \quad (1)$$

where $\left(P_x^{(k)\prime}, P_y^{(k)\prime}, P_z^{(k)\prime}\right)^T = R_j(P_x^{(k)}, P_y^{(k)}, P_z^{(k)})^T + t_j$ In equation (1), A represents known coefficients of the camera 12 capturing the image $I_j$. The unknown elements in equation (1) are the three-dimensional coordinates $(P_x^{(k)}, P_y^{(k)}, P_z^{(k)})$, the rotation matrix $R_j$, and the horizontal displacement $t_j$. Equation (1) shows the relationship between the three-dimensional coordinates of points in the standard three-dimensional model M of the user and the corresponding two-dimensional coordinates of the points. However, if we wish to know the three-dimensional coordinates of a point and we only know the two-dimensional coordinates of the point, then this is not enough information. In this case, it would be necessary to have the two-dimensional coordinates of the point in at least two images.

Similarly, when the camera 12 captures image $I_i$, the two-dimensional coordinates of $P^{(k)}$ are $(p_{i,x}^{(k)}, p_{i,y}^{(k)})$. The three-dimensional coordinates of point $P^{(k)}$ are equal to $(P_x^{(k)}, P_y^{(k)}, P_z^{(k)})$ and the two-dimensional model $(p_{i,x}^{(k)}, p_{i,y}^{(k)})$ of point $P^{(k)}$ satisfy the relationship given in equation (2):

$$\left(P_{i,x}^{(k)}, P_{i,y}^{(k)}, 1\right) = A\left(\frac{P_x^{(k)\prime}}{P_z^{(k)\prime}}, \frac{P_y^{(k)\prime}}{P_z^{(k)\prime}}, 1\right)^T, \quad (2)$$

where $\left(P_x^{(k)\prime}, P_y^{(k)\prime}, P_z^{(k)\prime}\right)^T = R_i(P_x^{(k)}, P_y^{(k)}, P_z^{(k)})^T + t_i$ If we pick N points $\{P^{(k)}\}_{k=k_1}^{k_N}$ from the standard three-dimensional model M of the user, where N≥8, and if we already know the two-dimensional coordinates of these N points in images $I_i$ and $I_j$, then we can use equation (1) and equation (2) to calculate the three-dimensional coordinates of the N points in the standard three-dimensional model M of the user, in which the image $I_i$ has the rotation $R_i$ and the horizontal displacement $t_i$, and the image $I_j$ has the rotation $R_j$ and the horizontal displacement $t_j$. This is preferably calculated using N=95 for the 95 feature points chosen. If only using these two images $I_i$ and $I_j$ to calculate the three-dimensional coordinates, the difference between the two images $I_i$ and $I_j$ ill be very large. Thus, the present invention preferably uses ten captured images at a time in order to more accurately calculate the standard three-dimensional model M of the user. The 95 feature points of the standard three-dimensional model M of the user already include the information needed for the standard three-dimensional model M of the user. Therefore, according to the 95 feature points and the shared facial features among the selected images, we can easily calculate the three-dimensional coordinates of other points in the images. There may be small errors for other points besides the 95 chosen feature points, but this will only have a minor impact on the overall calculations.

After finishing calculating the standard three-dimensional model M of the user, for any image $I_j$ once we have obtained the 95 feature points for image $I_j$ we can use equation (1) to quickly calculate the value $R_jM+t_j$ for the user's face in that image $I_j$. Furthermore, since we now know the value $R_jM+t$, we can accurately calculate the three-dimensional position of the superimposed virtual eyeglasses as well as the relationship between the three-dimensional superimposed virtual eyeglasses and the standard three-dimensional model M of the user. Based on the aperture of the camera 12, we can get the accurate position of the virtual eyeglasses in image $I_j$.

Figure 7:
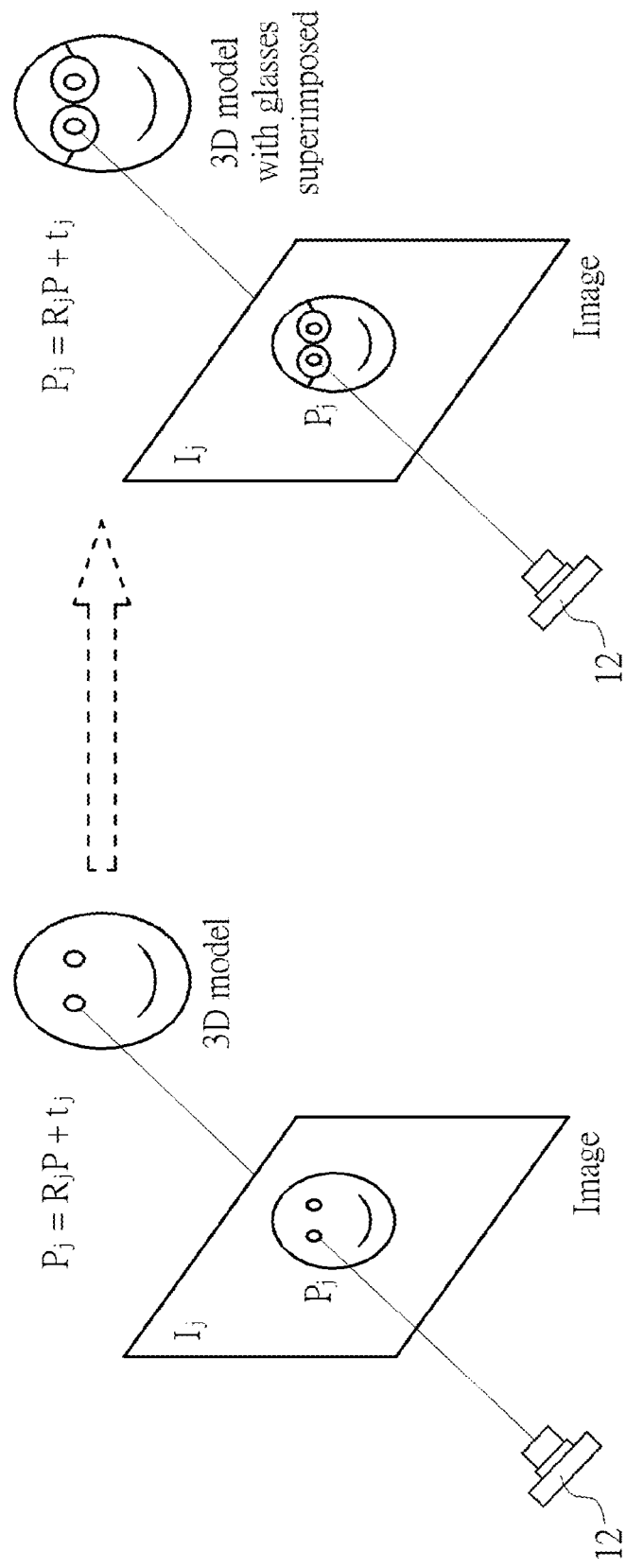
FIG. 7 illustrates how the selected pair of virtual eyeglasses is superimposed on the user's face using the standard three-dimensional model of the user.

Please refer to FIG. 7. FIG. 7 illustrates how the selected pair of virtual eyeglasses is superimposed on the user's face using the standard three-dimensional model M of the user. In FIG. 7 the standard three-dimensional model M of the user is modified by superimposing the three-dimensional model of the selected pair of virtual eyeglasses in order to create the modified three-dimensional model of the user having the selected pair of virtual eyeglasses superimposed thereon. In this way, the user can see how the selected pair of virtual eyeglasses would look on the user.

Figure 8:
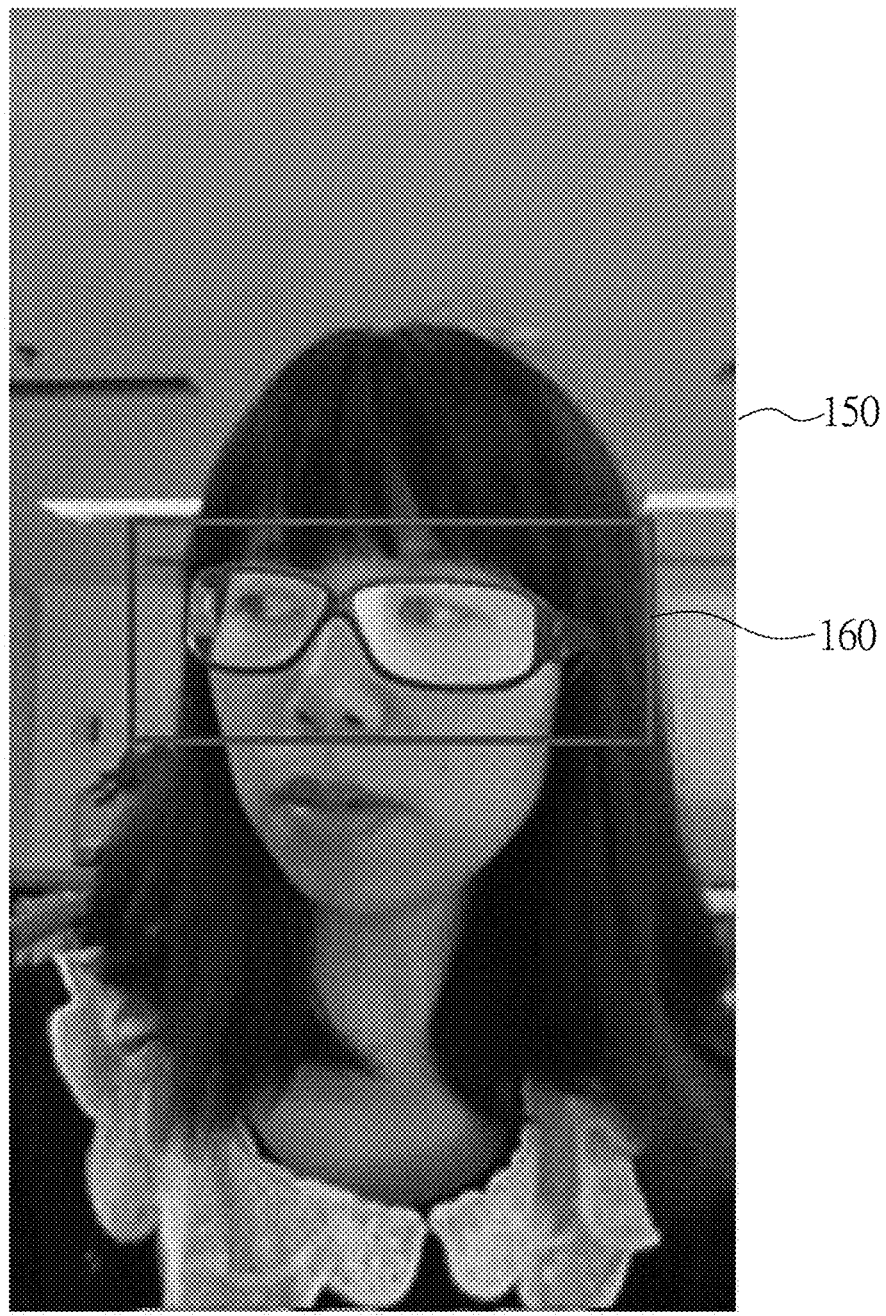
FIG. 8 shows an image in which the selected pair of virtual eyeglasses is superimposed on the user.
Figure 9:
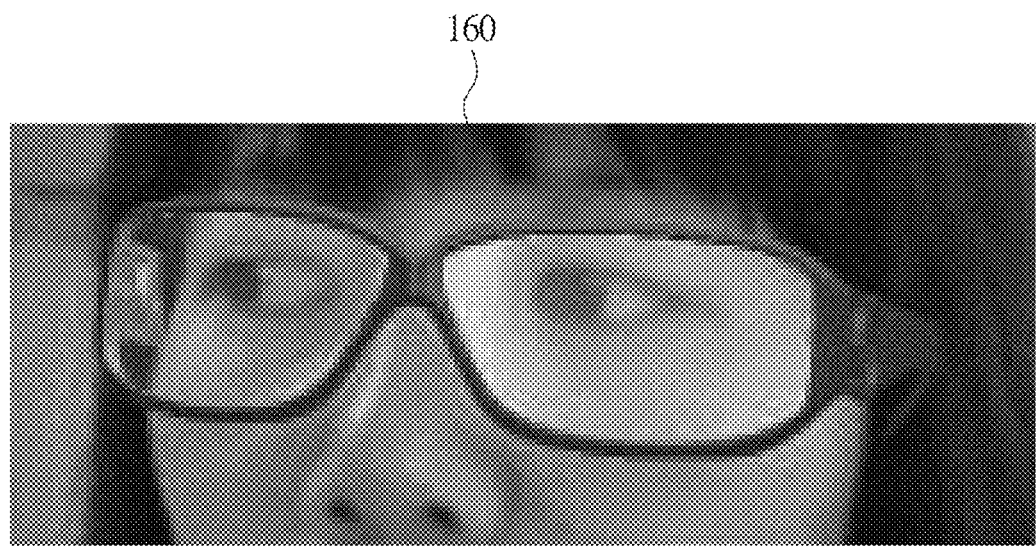
FIG. 9 shows a close-up image of the image shown in FIG. 8.
Figure 10:
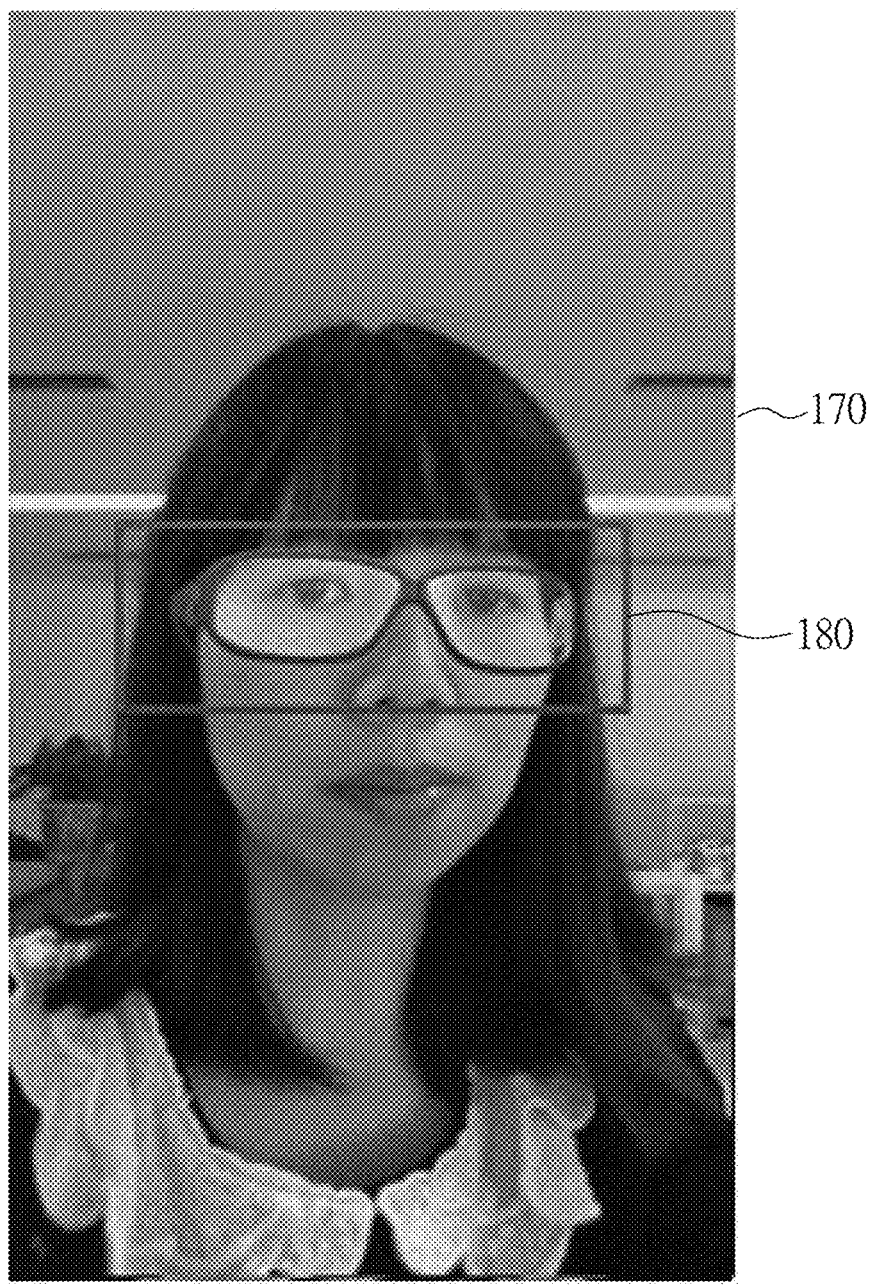
FIG. 10 shows another image in which the selected pair of virtual eyeglasses is superimposed on the user.
Figure 11:
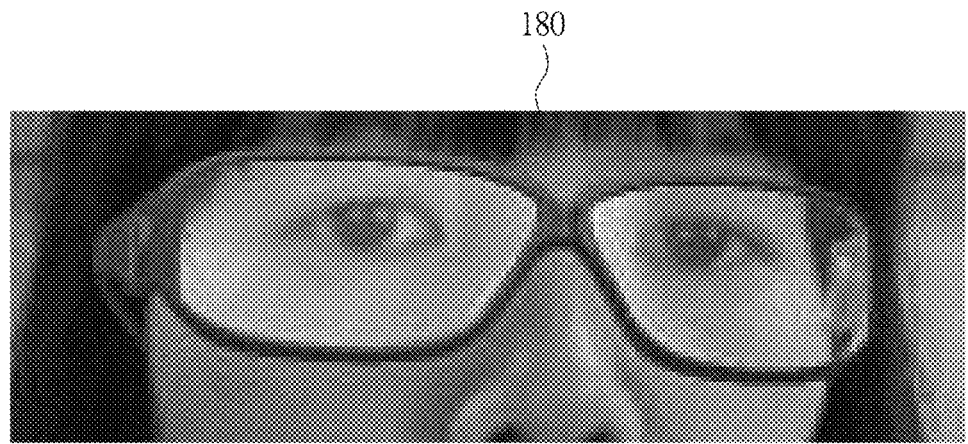
FIG. 11 shows a close-up image of the image shown in FIG. 10.

Please refer to FIGS. 8-11. FIG. 8 shows an image 150 in which the selected pair of virtual eyeglasses is superimposed on the user. FIG. 9 shows a close-up image 160 of the image 150 shown in FIG. 8. FIG. 10 shows another image 170 in which the selected pair of virtual eyeglasses is superimposed on the user. FIG. 11 shows a close-up image 180 of the image 170 shown in FIG. 10. The use of the standard three-dimensional model M of the user and the three-dimensional model of the selected pair of virtual eyeglasses makes these images 150 and 170 very realistic looking, and provides the user with a clear view of how the selected pair of virtual eyeglasses would look on the user. Please notice that depending on the angle of rotation of the user's face, one or more of the temples of the frame of the selected pair of virtual eyeglasses may be hidden, or blocked, by the user's face. By using three-dimensional models of both the user's face and the selected pair of virtual eyeglasses, this blocking relationship can be accurately depicted for making the resulting superimposed image very realistic looking.

Figure 12:
FIGS. 12-14 respectively depict images taken of a user with the camera as the user rotates his head.
Figure 13:
Figure 14:

Please refer to FIGS. 12-14, which respectively depict images 200, 210, and 220 taken of a user with the camera 12 as the user rotates his head. The camera 12 can either film a video of the user or capture a series of still images of the user in order to produce the sequence of captured images. In either case, when capturing the plurality of images of the user's face, preferably the user maintains a same facial expression in each image as the user's face is rotated while the position of the camera 12 is fixed. These images taken of the user's face from different rotation angles allow the standard three-dimensional model M of the user to be calculated.

Figure 15:
FIGS. 15-17 respectively depict images showing the selected pair of virtual eyeglasses being superimposed on the user.
Figure 16:
Figure 17:
Figure 18:
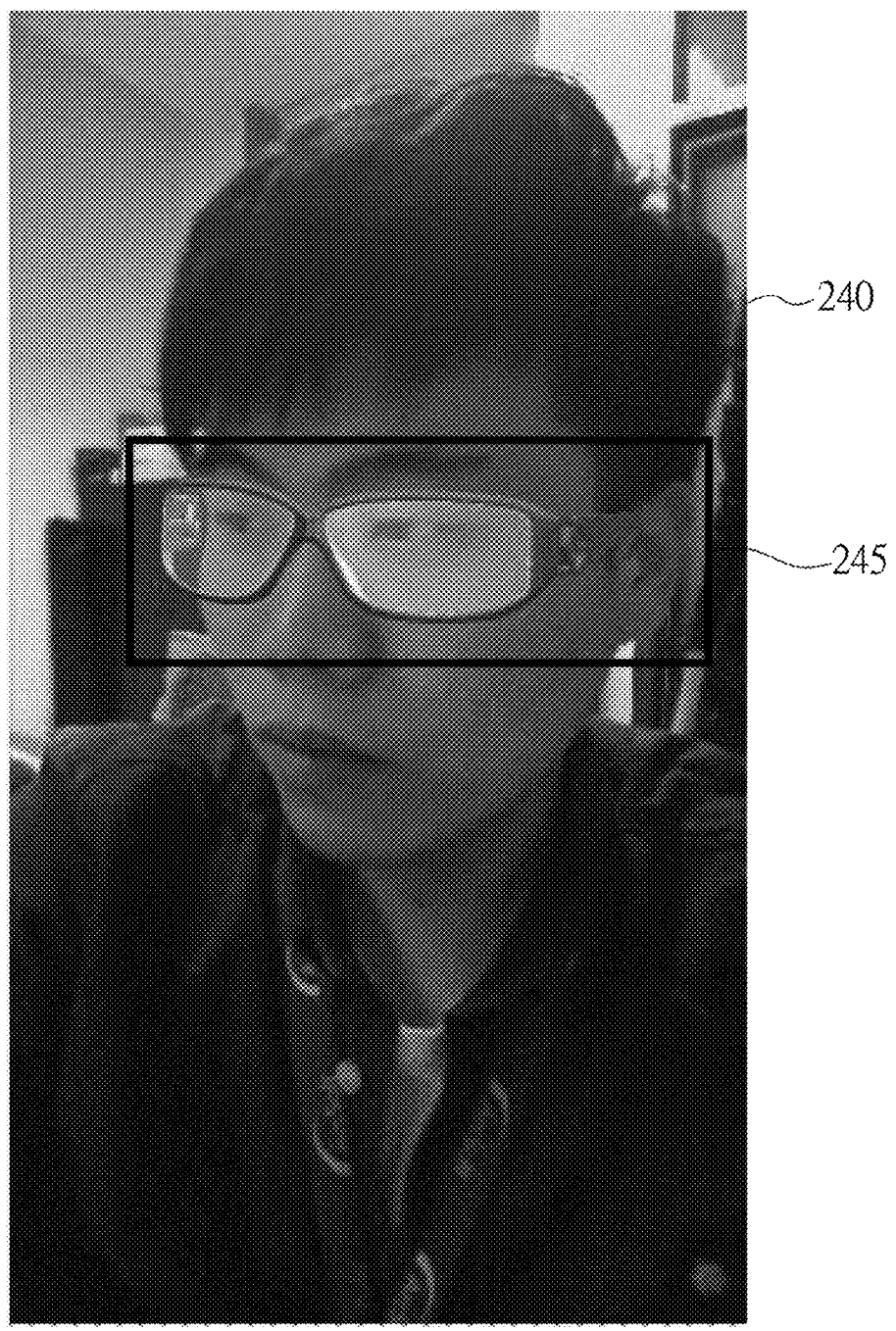
FIG. 18 shows the image shown in FIG. 16.
Figure 19:
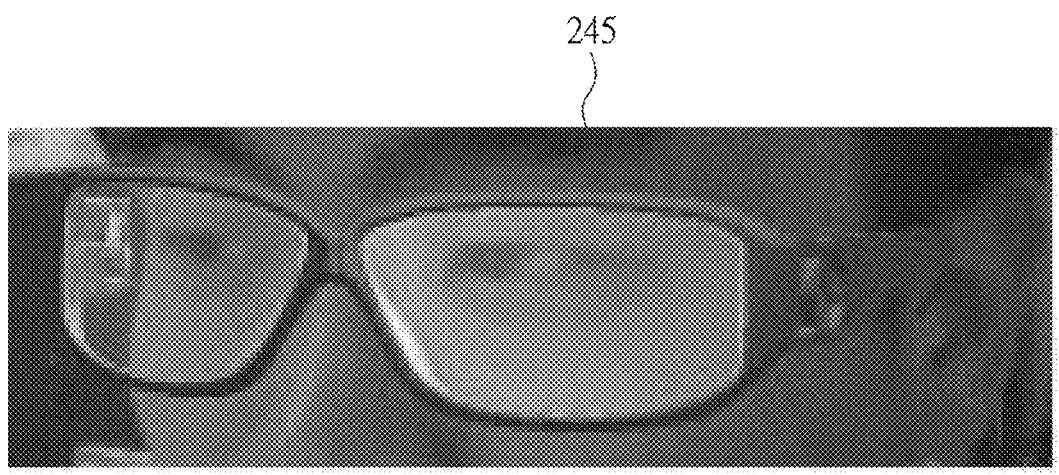
FIG. 19 shows a close-up image of the image shown in FIG. 18.
Figure 20:
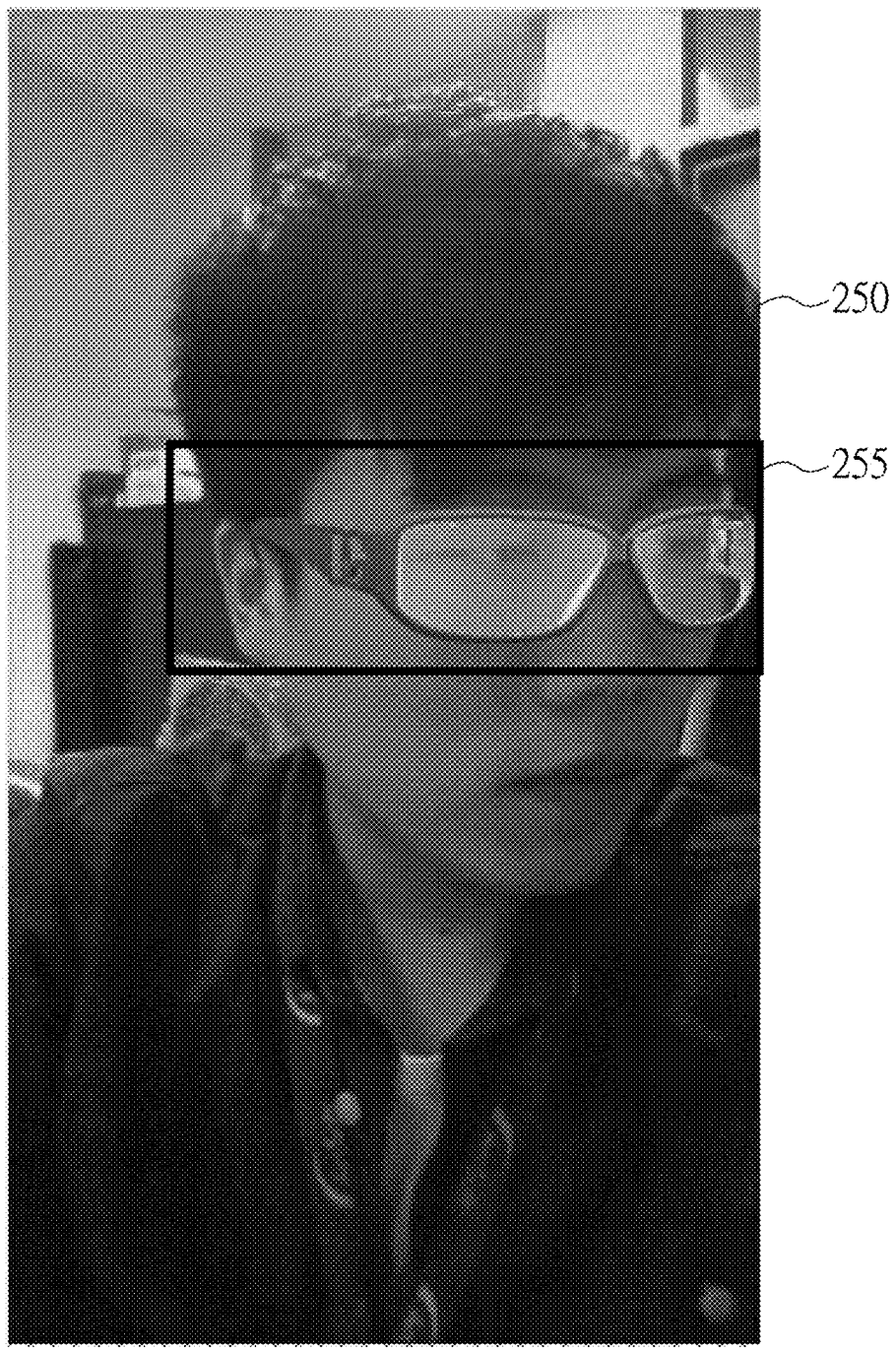
FIG. 20 shows the image shown in FIG. 17.
Figure 21:
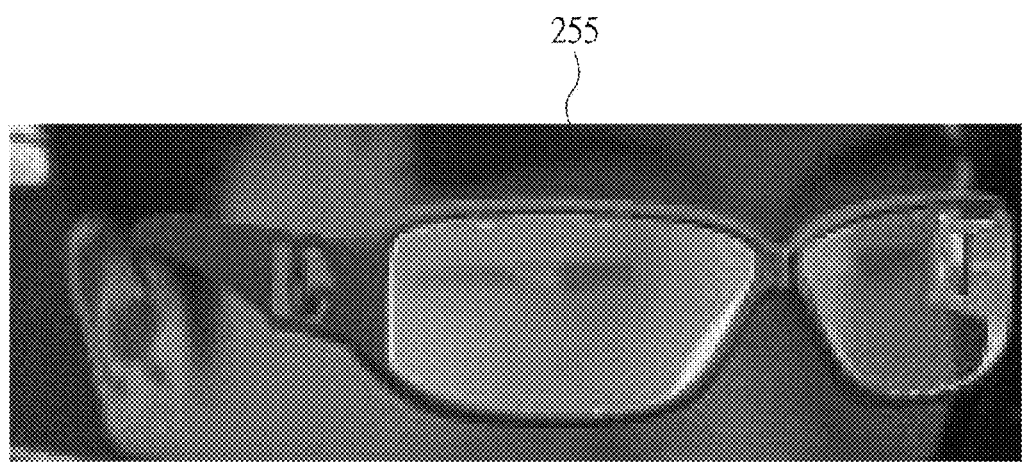
FIG. 21 shows a close-up image of the image shown in FIG. 20.

Please refer to FIGS. 15-17, which respectively depict images 230, 240, and 250 showing the selected pair of virtual eyeglasses being superimposed on the user. Image 230 shown in FIG. 15 corresponds to image 200 shown in FIG. 12, image 240 shown in FIG. 16 corresponds to image 210 shown in Fig. 13, and image 250 shown in Fig. 17 corresponds to image 220 shown in FIG. 14. Please refer to FIGS. 18-21. FIG. 18 shows the image 240 shown in FIG. 16, FIG. 19 shows a close-up image 245 of the image 240 shown in FIG. 18, FIG. 20 shows the image 250 shown in FIG. 17, and FIG. 21 shows a close-up image 255 of the image 250 shown in FIG. 20. Once the user chooses the selected pair of virtual eyeglasses, the selected pair of virtual eyeglasses can quickly be superimposed on the user's face.

Figure 22:
FIGS. 22-24 respectively depict images of a different pair of virtual eyeglasses chosen by the user.
Figure 23:
Figure 24:

Please refer to FIGS. 22-24, which respectively depict images 260, 270, and 280 of a different pair of virtual eyeglasses chosen by the user. Since the three-dimensional models of the virtual eyeglasses are built in advance, the user can easily switch from one pair of virtual eyeglasses to another to see how each pair looks on the user.

In summary, the present invention provides a way for the user to virtually try on different styles of eyeglasses without actually having to travel to an eyeglasses store. This allows the user to shop online for eyeglasses, thereby saving the user a considerable amount of time and also enabling the user to browse a much larger selection of different eyeglasses styles and sizes than available in traditional brick and mortar eyeglasses stores. Furthermore, by using three-dimensional modeling, the user will be given a chance to see exactly how the eyeglasses will look on the user. The present invention can be applied to any type of eyeglasses, including sunglasses, prescription eyeglasses, eyeglasses containing no lenses, and eyeglasses containing no prescription lenses.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of virtually trying on eyeglasses, the method comprising:

capturing a plurality of images of a user's face;

obtaining locations of a plurality of feature points on the user's face in the plurality of images;

using the locations of the plurality of feature points in the plurality of images to create a standard three-dimensional model of the user;

receiving selection from the user of a pair of virtual eyeglasses, the selected pair of virtual eyeglasses having a corresponding three-dimensional model depicting the size and shape of the selected pair of virtual eyeglasses;

creating a modified three-dimensional model of the user having the selected pair of virtual eyeglasses superimposed on the user's face according to the standard three-dimensional model of the user and the corresponding three-dimensional model of the selected pair of virtual eyeglasses; and displaying the resulting modified three-dimensional model of the user having the selected pair of virtual eyeglasses superimposed on the user's face;

wherein the position of the user's face in image $I_j$ is calculated as $R_j M + t_j$, where $R_j$ represents the rotation of the user's face in image $I_j$ and $t_j$ represents the horizontal displacement of the user's face in image $I_j$;

wherein the three-dimensional coordinates of a point $P^{(k)}$ is equal to $(P_x^{(k)}, P_y^{(k)}, P_z^{(k)})$; and wherein two-dimensional coordinates of point $P_j^{(k)}$ in image $I_j$ are calculated according to the equation $$\left(P_{j,x}^{(k)}, P_{j,y}^{(k)}, 1\right) = A \left(\frac{P_x^{(k)'}}{P_z^{(k)'}}, \frac{P_y^{(k)'}}{P_z^{(k)'}}, 1\right)^T,$$

in which updated coordinates of the coordinates $(P_x^{(k)}, P_y^{(k)}, P_z^{(k)})$ in image $I_j$ are calculated according to the equation $(P_x^{(k)'}, P_y^{(k)'}, P_z^{(k)'})^T = R_j (P_x^{(k)}, P_y^{(k)}, P_z^{(k)})^T + t_j$, where A represents known coefficients of a camera capturing the image $I_j$ and T indicates a matrix transpose function for reflecting a matrix over its main diagonal.

2. The method of claim 1, wherein when capturing the plurality of images of a user's face, the user's face is rotated for depicting the user's face with different angles of rotation in the plurality of images.

3. The method of claim 2, wherein the user's face maintains a same expression as the user's face is rotated.

4. The method of claim 1, wherein obtaining locations of the plurality of feature points on the user's face in the plurality of images comprises obtaining locations of eight or more feature points on the user's face in the plurality of images.

5. The method of claim 1, wherein obtaining locations of the plurality of feature points on the user's face in the plurality of images comprises obtaining locations of approximately 95 feature points on the user's face in the plurality of images.

6. The method of claim 1, wherein positions of the plurality of feature points are selected from a group consisting of outer edges of the eyes, outer edges of the mouth, outer edges of the nose, outer edges of the eyebrows, and outer edges of the face.

7. The method of claim 1, wherein capturing the plurality of images of the user's face comprises capturing ten or more images of the user's face.

8. The method of claim 1, wherein the standard three-dimensional model of the user is calculated as $M = \{P^{(k)}\}_{k=1}^{n}$, where M represents the standard three-dimensional model of the user, P represents three-dimensional coordinates of an individual feature point of the plurality of feature points, n represents the total number of the plurality of feature points, and k is an integer incremented from 1 to n.

9. The method of claim 1, wherein in the modified three-dimensional model of the user having the selected pair of virtual eyeglasses superimposed on the user's face, superimposing comprises hiding a temple of the selected pair of virtual eyeglasses when the temple would be blocked by the user's face as the user's face is rotated.

10. The method of claim 1, further comprising:
receiving selection from the user of a different pair of virtual eyeglasses, the different pair of virtual eyeglasses having a corresponding different three-dimensional model depicting the size and shape of the different pair of virtual eyeglasses; and
creating an updated modified three-dimensional model of the user having the different pair of virtual eyeglasses superimposed on the user's face according to the standard three-dimensional model of the user and the corresponding different three-dimensional model of the different pair of virtual eyeglasses.

\* \* \* \* \*